United States Patent [19]

Suzuki et al.

[11] Patent Number: 5,171,471
[45] Date of Patent: Dec. 15, 1992

[54] DIOXANE LIQUID CRYSTAL COMPOUNDS

[75] Inventors: Yoshiichi Suzuki; Takashi Hagiwara; Koichi Numazawa, all of Tokyo, Japan

[73] Assignee: Showa Shell Sekiyu K.K., Tokyo, Japan

[21] Appl. No.: 831,195

[22] Filed: Jan. 31, 1992

Related U.S. Application Data

[63] Continuation-in-part of Ser. No. 794,855, Nov. 21, 1991, abandoned, which is a continuation of Ser. No. 321,245, Mar. 9, 1989, abandoned.

[30] Foreign Application Priority Data

Mar. 9, 1988 [JP] Japan .................................. 63-53805

[51] Int. Cl.$^5$ ............... C09K 19/34; C09K 19/12; C09K 19/20; C09K 19/52; C07D 219/01
[52] U.S. Cl. .................. 252/299.61; 252/299.64; 252/299.65; 252/299.66; 252/299.67; 252/299.01; 549/375
[58] Field of Search ........... 252/299.4, 299.61, 299.63, 252/299.64, 299.67, 299.65, 299.66; 359/103, 104; 549/375; 560/76, 87, 107, 111

[56] References Cited

U.S. PATENT DOCUMENTS

| | | | |
|---|---|---|---|
| 4,753,752 | 1/1988 | Raynes et al. | 252/299.65 |
| 4,894,181 | 1/1990 | Praefcke et al. | 252/289.61 |
| 4,961,876 | 10/1990 | Demus et al. | 252/299.67 |
| 4,973,738 | 11/1990 | Suzuki et al. | 252/299.6 |

FOREIGN PATENT DOCUMENTS

| | | |
|---|---|---|
| 1-139576 | 6/1989 | Japan . |
| 1139567 | 6/1989 | Japan . |
| 227706 | 9/1985 | Netherlands . |
| 227719 | 9/1985 | Netherlands . |

Primary Examiner—Robert L. Stoll
Assistant Examiner—Shean C. Wu
Attorney, Agent, or Firm—Sughrue, Mion, Zinn, Macpeak & Seas

[57] ABSTRACT

Novel ferroelectric and antiferroelectric liquid crystal compounds of the invention, which comprise those showing optically tristable states in phase $S^*_{(3)}$, have a wide range of phase transition temperature so as to be not only preferably used solely as display element material but also mixed with any other liquid crystal to desiredly expand the above range wider and make optical response time faster.

Typical compounds are represented by

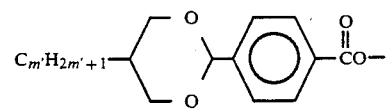

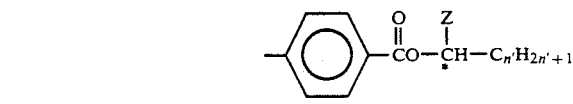

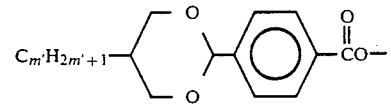

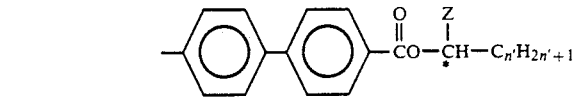

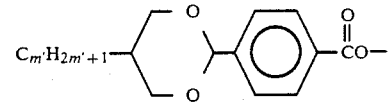

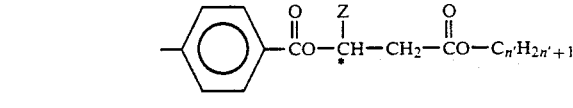

in which Z means $CF_3$, $C_2F_5$, $CHF_2$, $CH_2F$, $CClF_2$, $CCl_2F$, $CF_3CCl_2$ or $C_3F_7$, $m'$ and $n'$ are same or different with each other and each is an integer of 1-20.

9 Claims, 6 Drawing Sheets

DIOXANE LIQUID CRYSTAL COMPOUNDS

This is a continuation-in-part application of U.S. Ser. No. 07/794,855 filed Nov. 21, 1991, now abandoned, which is a continuation application of U.S. Ser. No. 07/321,245 filed Mar. 9, 1989 now abandoned.

DESCRIPTION OF THE PRIOR ART

The invention relates to liquid crystal compounds having a dioxane ring. It relates particularly to smectic and ferroelectric dioxane liquid crystal compounds, and more particularly to antiferroelectric dioxane liquid crystal compounds having $S^*_{(3)}$ phase in which optically tristable states are shown.

Liquid crystal display elements have been widely used in twisted nematic (TN) mode, guest-host (GH) mode and so on owing to the excellent properties thereof such as low voltage actuability, low energy consumption, displayability in a thin structure and so on.

The liquid crystal display elements of the nematic type, however, are disadvantageous in that slow speed of response in the order of several milli-second to several ten milli-second so that there are considerable limitations in the applied uses thereof.

In order to solve the problem referred to above, a satelite tracking network (STN) mode has been developed, but it is still unsatisfactory in that it is necessary to precisely control a cell gap and a tilt angle and in that the time response is still low, despite of that display properties such as a display contrast and a viewing angle have been considerably improved.

In order to comply with demands for novel liquid crystal displays superior in the response time, ferroelectric liquid crystals were developed so as to provide liquid crystal devices having the far faster optical response time in the order of $\mu$sec.

In the year of 1975, p-decyloxybenzilidene-p-amino-2-methylbutylcinamate (DOBAMBC) was synthesized as the ferroelectric liquid crystal by Meyer et al., and in the year of 1980 the high speed switching and memory properties of DOBAMBC were confirmed by Clark and Longwall (N. A. Clark et al., Appl. Phys. Lett. 36, 899 (1980)) so as to attract attentions as an epoch-making liquid crystal element material capable of realizing the moving image display of a large picture in the simple matrix mode.

However, there were still technical problems so as to actually use the above ferroelectric liquid crystal. Above all, satisfactory ferroelectricity at the room temperature and satisfactory control of orientation of the liquid crystal molecules which is necessary for the display device could not be attained.

The inventors have found some antiferroelectric liquid crystal compounds having $S^*_{(3)}$ phase in which optically tristable states are shown. The antiferroelectric liquid crystal compounds in $S^*_{(3)}$ phase have definite threshold value and hysteresis properties relative to driving voltage so as to realize large moving picture display according to the simple matrix mode and a novel electrooptical shutter owing to the particular electroclinic effect thereof, which is disclosed in A. D. L. Chandani, T. Hagiwara, Y. Suzuki, et al., Japan J. of Appl. Phys., 27 (5), 729-732 (1988), and JP-A Sho 63 (1988)-21159 and 21160.

SUMMARY OF THE INVENTION

It is an object of the invention, thus, to provide novel ferroelectric liquid crystal compounds and further novel antiferroelectric liquid crystal compounds having $S^*_{(3)}$ phase in a wider range of temperatures inclusive of the room temperature.

The above objects can be attained by a certain scope of compounds, each having a dioxane ring as the heterocyclic ring as definitely defined in the Claims.

DETAILED DESCRIPTION OF THE INVENTION

Figure 1:
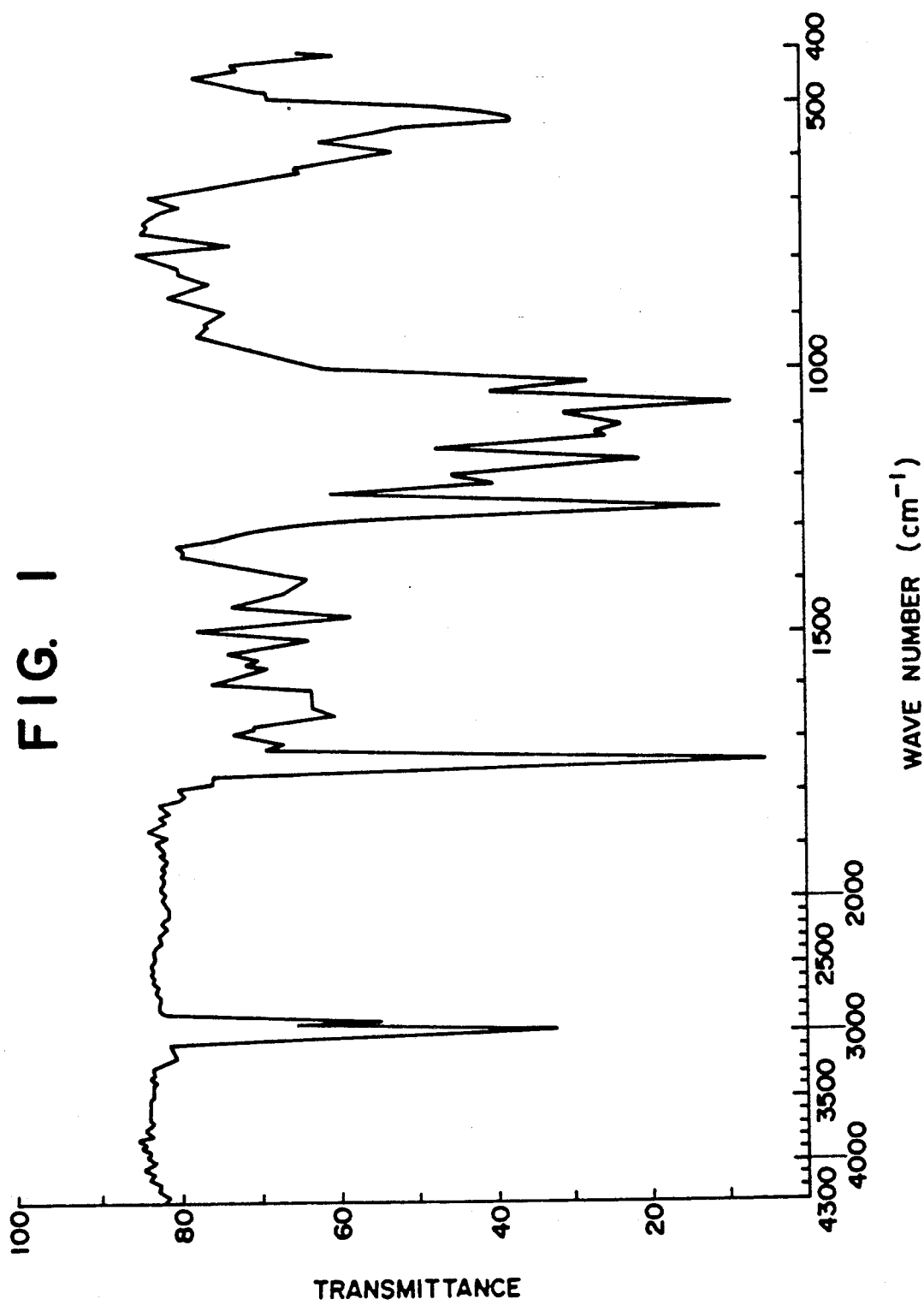
FIG. 1 shows an infrared absorption spectrum (KBr) of (R)-(+)-4'-(1-trifluoromethylnonyloxycarbonyl)-1-phenyl 4-(5-n-pentyl-trans-1,3-dioxane-2-yl)benzoate, the objective compound in Example 1.

The invention relates to liquid crystal compounds represented by the general formula (I)

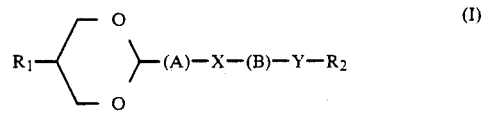

$R_1$ means an alkyl, alkoxy, alkyloxycarbonyl of alkylcarbonyloxy group having 1-20 carbon atoms, preferably $C_nH_{2n+1}$, $C_nH_{2n+1}O$,

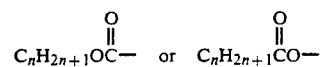

wherein n is an integer of 5-10, and more preferably an alkyl group such as pentyl ($C_5H_{11}$), octyl ($C_8H_{17}$), nonyl($C_9H_{19}$) or decyl($C_{10}H_{21}$) group.

(A) means

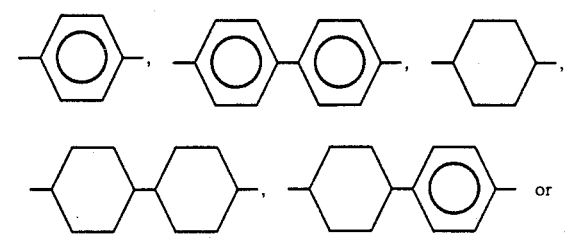

-continued

X means

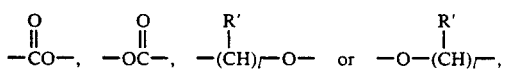

wherein R' is hydrogen or a lower alkyl such as methyl and ethyl, and l is an integer of 1-16, preferably

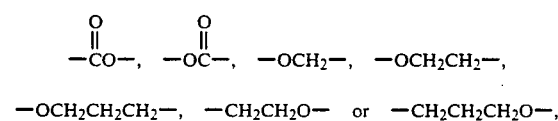

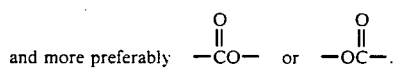

and more preferably (B) means

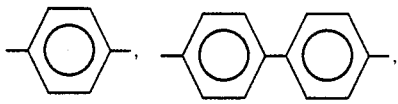

Y means

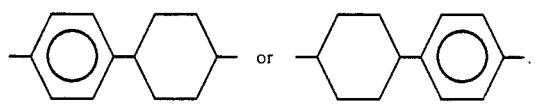

and preferably

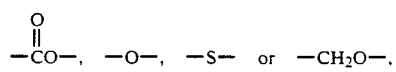

$R_2$ means

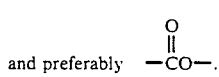

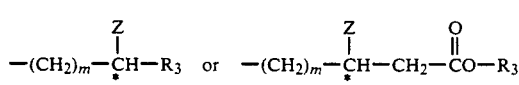

in which Z means $CF_3$, $C_2F_5$, $CHF_2$, $CH_2F$, $CClF_2$, $CCl_2F$, $CF_3CCl_2$ or $C_3F_7$, and preferably $CF_3$, $C_2F_5$ or $C_3F_7$; $R_3$ means a straight or branched alkyl, aralkyl, alkoxyalkyl, alkoxycarbonyl or alkoxycarbonylalkyl group of 1-20 carbon atoms, or a substituted vinyl, substituted cyclopropyl or substituted epoxy group, and m is an integer of 0-20 and preferably 0-10.

$R_2$ preferably means

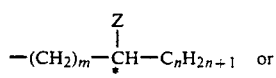

-continued

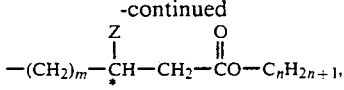

in which m and n mean respectively an integer of 0-10. The preferable group, $C_nH_{2n+1}$ is pentyl, hexyl, octyl, nonyl or decyl.

More definitely, $R_2$ is a radical derived from any of the following optically active alcohols;
1,1,1-trifluoro-2-$C_6$-$C_{16}$ alkanol,
1,1-difluoro-2-$C_6$-$C_{16}$ alkanol,
1-monofluoro-2-$C_6$-$C_{16}$ alkanol,
1,1,1,2,2-pentafluoro-3-$C_6$-$C_{16}$ alkanol,
1-monofluoro-1,1-dichloro-2-$C_6$-$C_{16}$ alkanol,
1,1,1-trichloro-2-$C_6$-$C_{16}$ alkanol,
1,1,1-trifluoromethyl-1-phenylmethanol,
1,1,1-trifluoromethyl-2-phenylethanol,
1,1,1-trifluoromethyl-3-phenylpropanol,
1,1,1-trifluoro-3-decene-2-al,
1,1,1-trifluoro-3-heptene-2-al,
methyl-4,4,4-trifluoro-3-hydroxybutylate,
ethyl-4,4,4-trifluro-3-hydroxybutylate,
propyl-4,4,4-trifluoro-3-hydroxybutylate,
butyl-4,4,4-trifluoro-3-hydroxybutylate,
pentyl-4,4,4-trifluoro-3-hydroxybutylate,
hexyl-4,4,4-trifluoro-3-hydroxybutylate,
heptyl-4,4,4-trifluoro-3-hydroxybutylate,
octyl-4,4,4-trifluoro-3-hydroxybutylate,
nonyl-4,4,4-trifluoro-3-hydroxybutylate, and
decyl-4,4,4-trifluoro-3-hydroxybutylate.

The haloalcohols may be manufactured according to disclosures in e.g. "J. Org. Chem." 52, (15), 3211 (1987) and "Science" 56 (9), 531 (1986).

Particularly preferably liquid crystal compounds of the invention are represented by the formula (I), in which $R_1$ means an alkyl, alkoxy, alkylalkoxycarbonyl or alkylcarbonyloxy group of 4-20 carbon atoms, preferably $C_nH_{2n+1}$, $C_nH_{2n+1}O$,

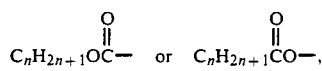

and more preferably a straight chain alkyl or $C_nH_{2n+1}$ in which n is an integer of 5-10;

(A) means

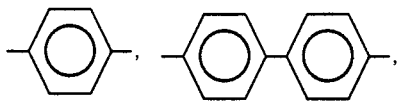

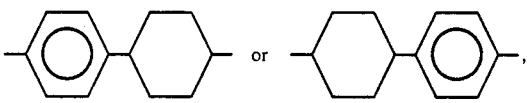

X means

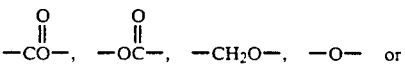

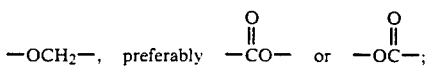

(B) means

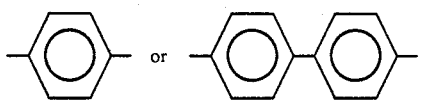

Y means

—O—, —S— or —CH$_2$O—; and
R$_2$ means

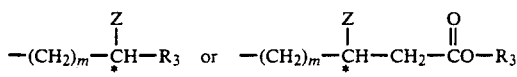

wherein Z is CF$_3$, C$_2$F$_5$, CHF$_2$, CH$_2$F, CClF$_2$, CCl$_2$F, CF$_3$CCl$_2$ or C$_3$F$_7$, preferably CF$_3$, C$_2$F$_5$ or C$_3$F$_7$; R$_3$ means a straight or branched alkyl or 3-15 carbon atoms; and m is an integer of 0-15, preferably 0-10, and R$_2$ more preferably means

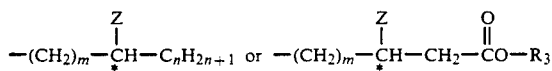

wherein C$_n$H$_{2n+1}$ is pentyl, hexyl, octyl, nonyl or decyl and derived from the optically active alcohols comprising 1,1,1-trifluoro-2-C$_6$-C$_{16}$ alkanol; 1,1-difluoro-2-C$_6$-C$_{16}$ alkanol; 1-monofluoro-2-C$_6$-C$_{16}$ alkanol; 1,1,1,2,2-pentafluoro-3-C$_6$-C$_{16}$ alkanol; 1-monofluoro-1,1-dichloro-2-C$_6$-C$_{16}$ alkanol; 1,1,1-trichloro-2-C$_6$-C$_{16}$ alkanol; and 1,1-difluoro-1-monochloro-2-C$_6$-C$_{16}$ alkanol.

Among the novel liquid crystal compounds of the invention represented by the formula (I), wherein R$_1$ is an alkyl, alkoxy, alkyloxycarbonyl or alkylcarbonyloxy group of 5-20 carbon atoms, and preferably C$_n$H$_{2n+1}$ or C$_n$H$_{2n+1}$O, and more preferably C$_n$H$_{2n+1}$ in which n is an integer of 6-10.

(A) is

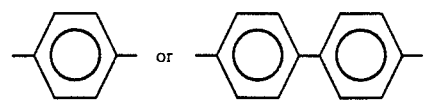

X is

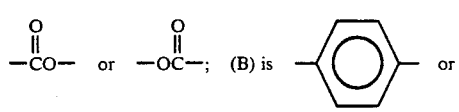

; (B) is  or

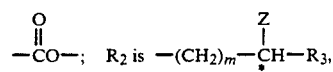

Y is

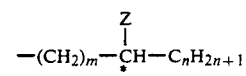

wherein Z means CF$_3$, C$_2$F$_5$, CHF$_2$, CH$_2$F, CClF$_2$, CCl$_2$F or CF$_3$CCl$_2$ more preferably CF$_3$ or C$_2$F$_5$; R$_3$ means a striaght or branched alkyl or 3-15 carbon atoms; and m is an integer of 0-3, preferably 0 or 1; R$_2$ is preferably $$-(CH_2)_m-\overset{Z}{\underset{*}{C}H}-C_nH_{2n+1}$$

in which C$_n$H$_{2n+1}$ preferably means
pentyl, hexyl, octyl, nonyl or decyl, which is derived from 1,1,1-trifluoro-2-C$_6$-C$_{16}$ alkanol, 1,1-difluoro-2-C$_6$-C$_{16}$ alkanol, 1-monofluoro-2-C$_6$-C$_{16}$ alkanol, 1,1,1,2,2-pentafluoro-3-C$_6$-C$_{16}$ alkanol, 1-monofluoro-1,1-dichloro-2-C$_6$-C$_{16}$ alkanol, 1,1,1-trichloro-2-C$_6$-C$_{16}$ alkanol and 1,1-difluoro-1-monochloro-2-C$_6$-C$_{16}$ alkanol, those show the tristable liquid crystal phase, The compounds of the invention may be manufactured as follows:

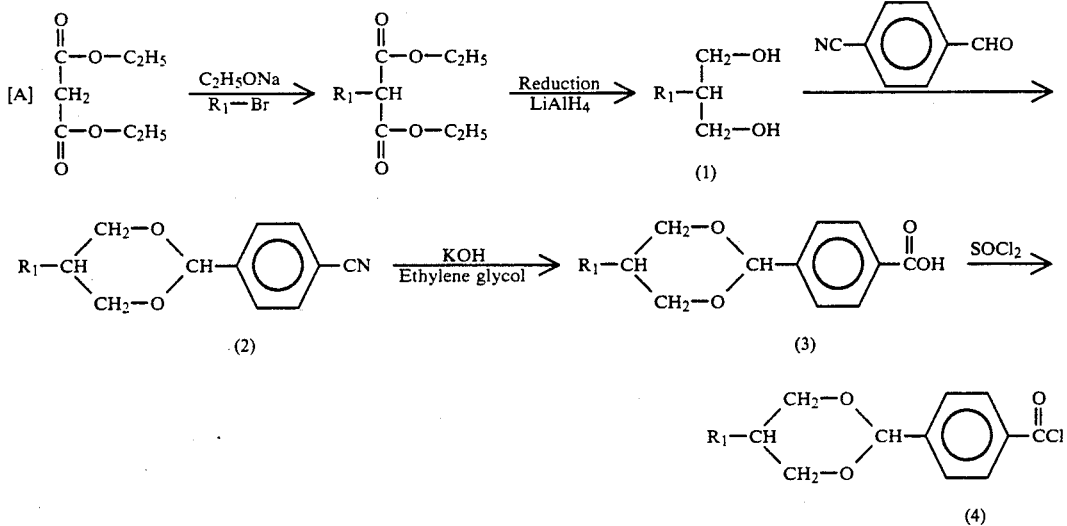

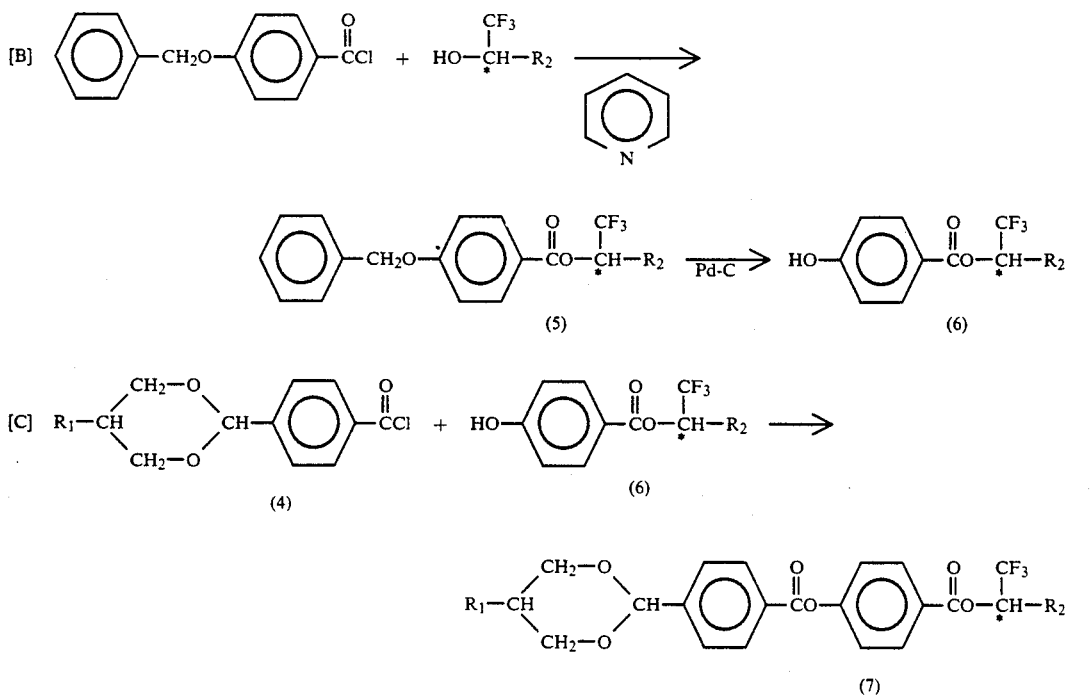

In the formula $R_1$ and $R_2$ mean the same as above.

(A) Ethyl malonate is allowed to react with a sodium alcoholate and an alkyl bromide to obtain a 2-alkyl-ethyl malonate, which is reduced in ether or tetrahydrofuran with hydrogenated lithium aluminum to obtain 2-alkyl-1,3-propanediol (1). The compound (1) is then allowed to react with 4'-cyanobenzaldehyde to obtain 2-(4'-cyanophenyl)-5-alkyl-1,3-dioxane (2), of which cyano group is hydrolyzed in the presence of caustic potash and ethylene glycol to obtain 2-(4'-carboxyphenyl)-5-alkyl-1,3-dioxane (3). The compound (3) is treated with thionylchloride to obtain the corresponding chloride (4).

(B) Meanwhile, 4-benzyloxy-benzoic acid chloride is added with optically active 1-trifluoromethyl-1-akanol in the presence of pyridine to obtain 1-trifluoromethyl-1-alkyl 4-benzyloxybenzoate (5), which is hydrogenated with using Pd/carbon as catalyst to obtain 1-trifluoromethyl-1-alkyl 4-hydroxybenzoate (6).

(C) Then the chloride (4) of the dioxane (3) is reacted with 1-trifluoromethyl-1-alkyl 4-hydroxybenzoate (6) to obtain the objective compound, 4'-(1-trifluoromethylalkyloxycarbonyl)-phenyl 4-(5-alkyl-1,3-dioxane-2yl)benzoate (7).

4'-Cyanobipheyl-4-aldehyde can be used in place of 4-cyanobenzaldehyde in (A). 4'-Benzyloxybiphenyl-4-carboxylic acid chloride can be used in place of 4-benzyloxybenzoic acid chloride in (B).

Now some Examples are to be given, but the invention is of course not limited thereto.

EXAMPLE 1

1) Synthesis of (R)-(+)-1-trifluoromethylnonyl 4-benzyloxybenzoate

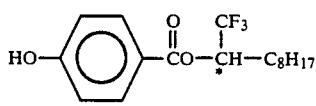

3.6 g of 4-Benzyloxy-benzoic acid chloride and 2.2 g of (R)-(+)-1,1,1-trifluoro-2-decanol ($[\alpha]_d = 22.3°$) were added in 35 ml of pyridine to be stirred at the room temperature for 12 hours and poured into ice-water and extracted with methylene chloride. The methylene chloride phase was washed successively with 1N sodium carbonate solution, water, diluted hydrochloric acid and water to recover the organic phase, which was dried over anhydrous magnesium sulphate, distilled to remove the solvent and subjected to toluene/silica gel chromatography to obtain the titled compound.

2) Synthesis of (R)-(+)-1-trifluoromethylnonyl 4-hydroxylbenzoate

HO—⟨⟩—CO—CH(CF$_3$)—C$_8$H$_{17}$

The compound obtained in 1) was dissolved in 50 ml of methanol, added with 0.2 g of 10% Pd/carbon catalyst and hydrogenated in an atmosphere of hydrogen under high pressure to obtain the titled compound.

3) Synthesis of (R)-(+)-4'-(1-trifluoromethylnonyloxycarbonyl)-phenyl 4-(5-n-pentyl-trans-1,3-dioxane-2-yl)benzoate

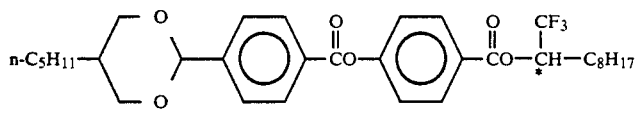

Thionyl chloride in the excessive amount was allowed to react with 4-(5-n-pentyl-trans-1,3-dioxane-2-yl)-benzoic acid, which was obtained by alkaline hydrolysis of usually synthesized 4-(5-pentyl-1,3-dioxane-2-yl)benzonitrile in the amount of 2.2 g in ethylene glycol as solvent, under reflux for 6 hours and distilled for removing unaltered thionyl chloride to obtain the acid chloride in an amount of 1.74 g.

(R)-(+)-1-trifluoromethylnonyl 4-hydroxybenzoate obtained in 2) in the amount of 1.52 g was reacted with the above acid chloride in an amount of 1.74 g in 20 ml of pyridine at the room temperature for a whole day and night. The reaction liquid was poured into ice-water and extracted with methylene chloride. The methylene chloride phase was successively washed with 1N sodium carbonate solution, water, diluted hydrochloric acid and water. The organic phase was dried over anhydrous magnesium sulphate and distilled for removing the solvent to obtain the crude objective compound.

The crude objective compound was subjected to toluene/silica gel chromatography to obtain the optically active compound ($[\alpha]_D= +28.9°$) in an amount of 1.1 g.

This liquid crystal compound of the invention shows following phase transition temperatures;

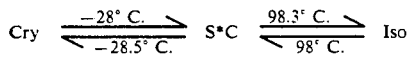

S*C means chiral smectic C phase, Cry means crystal phase and Iso means isotropic phase.

The infrared absorption spectrum (KBr) thereof is shown in FIG. 1.

EXAMPLE 2

1) Synthesis of 1-trifluoromethylheptyl 4-benzyloxybenzoate

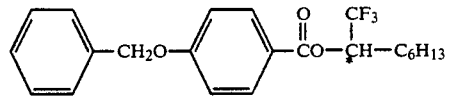

4-Benzyloxy-benzoic acid chloride in an amount of 4.3 g was dissolved in 50 ml of methylene chloride, to which a solution of 2.9 g of optically active 1,1,1-trifluoro-2-octanol, 0.6 g of dimethylaminopyridine and 1.7 g of triethylamine in 50 ml of methlene chloride was gradually added under cooling with ice.

The mixture was held at the room temperature for reaction for a whole day and night. The reaction liquid was taken in ice-water and extracted with methylene chloride. The methylene chloride phase was successively washed with diluted hydrochloric acid, water, 1N sodium carbonate solution and water, dried over anhydrous magnesium sulphate, and distilled for removing the solvent to obtain the crude compound captioned above, which was treated according to toluene/silica gel chromatography and recrystallized with ethanol to obtain the purified compound in an amount of 3.8 g.

2) Synthesis of 1-trifluoromethylheptyl 4-hydroxybenzoate

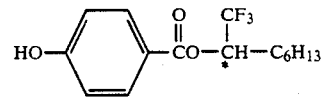

The compound obtained in 1) was dissolved in 100 ml of methanol. The solution was added with 10% Pd/carbon catalyst and hydrogenated in hydrogen atmosphere to obtain the titled compound in the amount of 2.8 g.

3) Synthesis of 4'-(1-trifluoromethylheptyloxycarbonyl)-phenyl 4-(5-n-nonyl-trans-1,3-dioxane-2-yl)benzoate

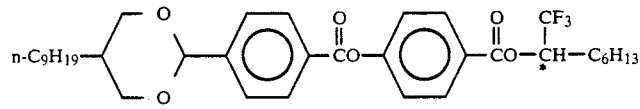

4-(5-Nonyl-trans-1,3-dioxane-2-yl)benzonitrile obtained according to the usual method was subjected to alkaline hydrolysis in ethylene glycol as solvent to obtain 4-(5-nonyl-trans-1,3-dioxy-2-yl)benzoic acid. This benzoic acid derivative in an amount of 0.700 g, 0.537 g of 1-trifluoromethylheptyl 4-hydroxybenzoate obtained in 2), 0.546 g of dicyclohexylcarbodiimide and a very small amount of dimethylaminopyridine were allowed to react in 30 ml of tetrahydrofuran at the room temperature for a whole day and night. The reaction mixture was filtered to remove the unsolved content and distilled in order to remove tetrahydrofuran. The residue was subjected to silica gel chromatography and recrystallized with ethanol to obtain the optically active objective compound in an amount of 0.179 g. The optical rotation thereof $[\alpha]_D^{20}= -30.47°$.

This objective liquid crystal compound shows following phase transition temperatures as a result of observation by means of the polarizing microscope with a hot stage.

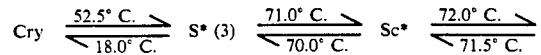

-continued

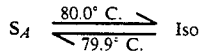

S*$_{(3)}$ means the liquid crystal phase in which the compound shows optically tristable states.

Figure 2:
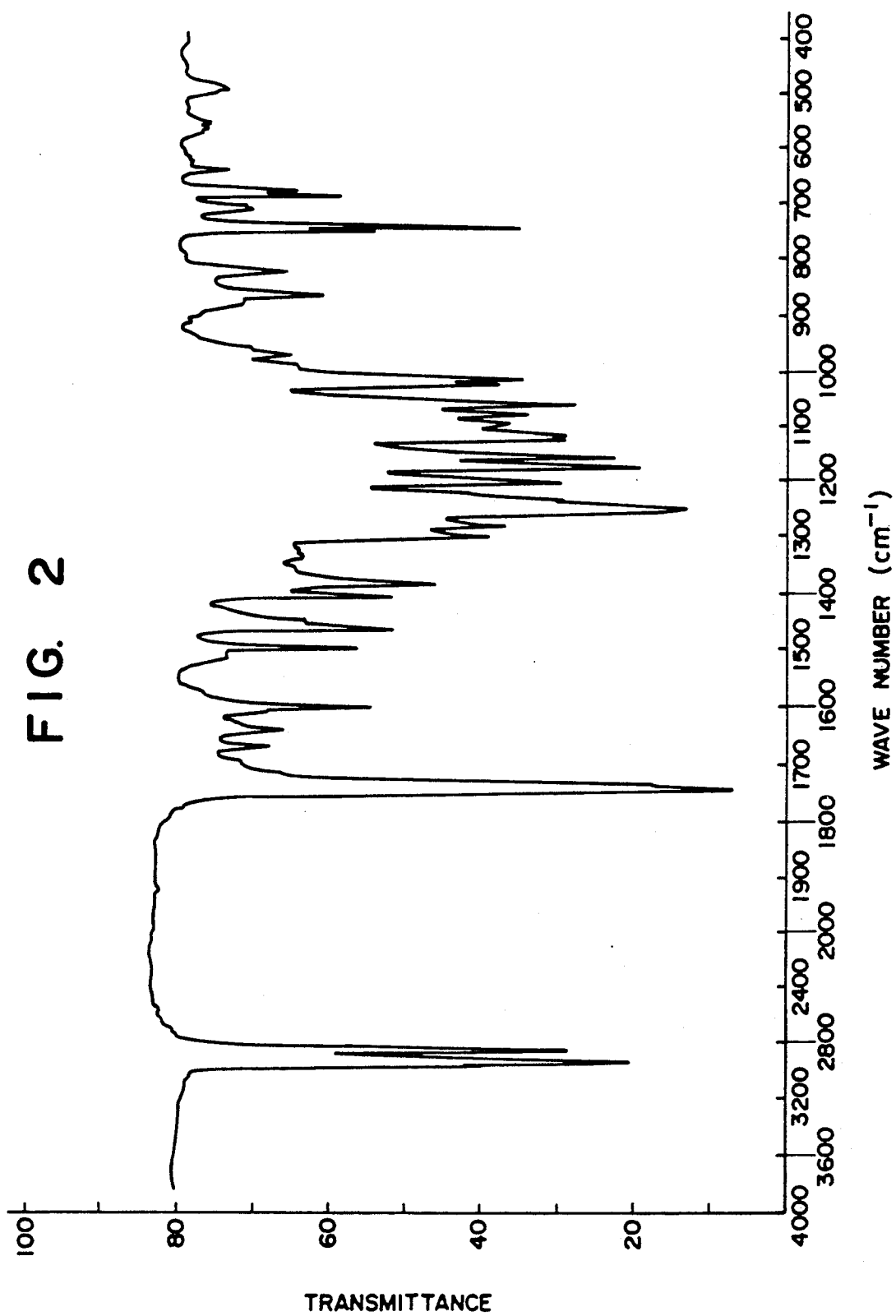
FIG. 2 shows the spectrum of 4'-(1-trifluoro-methyl-heptyloxycarbonyl)phenyl 4-(5-n-nonyl-trans-1,3-dioxane-2-yl)benzoate, the objective compound in Example 2.

The infrared absorption spectrum (KBr) thereof and the nuclear magnetic resonance spectrum are respectively shown in FIG. 2 and Table 1 given hereafter.

EXAMPLE 3

1) Synthesis of (R)-(+)-1-trifluoromethyl-2-ethoxycarbonylethyl 4-benzyloxybenzoate

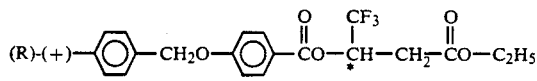

4-benzyloxybenzoyl chloride in the amount of 1.8 g was dissolved in 30 ml of methylene chloride to prepare a solution, to which a solution of 1.2 g of (R)-(+)-ethyl-4,4,4-trifluoro-2-hydroxybutylate ([α]$_D^{20}$= +21.80), 0.7 g of triethylamine and 0.2 g of dimethyl aminopyridine in 20 ml of methylene chloride was gradually added under cooling with ice, after which the reaction liquid was held at the room temperature to be stirred for 12 hours. The reaction liquid was poured into ice-water and extracted with methylene chloride. The methylene chloride phase was successively washed with diluted hydrochloric acid, water, 1N sodium carbonate solution and water so as to recover an organic phase, which was dried over anhydrous magnesium sulphate, distilled for removing the solvent and subjected to toluene/silica gel chromatography to obtain the titled compound in an amount of 1.1 g.

2) Synthesis of (R)-(+)-1-trifluoromethyl-2-ethoxycarbonylethyl 4-hydroxybenzoate

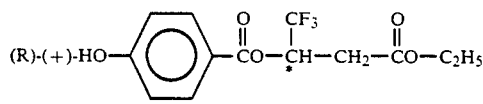

The compound obtained in 1) was dissolved in 50 ml of methanol, added with 10% Pd/carbon catalyst and hydrogenated in hydrogen atmosphere to obtain the titled compound in the amount of 0.8 g.

3) (R)-(+)-4-(1-trifluoromethyl-2-ethoxycarbonylethyloxycarbonyl)-phenyl 4-(5-n-pentyl-trans-1,3-dioxane-2-yl)benzoate

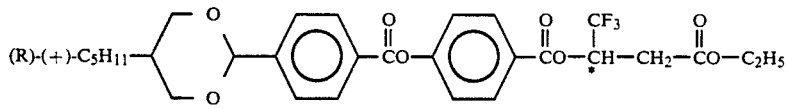

Separately, 1.2 g of 4-(5-pentyl-trans-1,3-dioxane-2-yl)benzonitrile prepared according to the usual method was subjected to alkaline hydrolysis with using ethylene glycol as solvent to obtain 4-(5-n-pentyl-trans-1,3-dioxane-2-yl)benzoic acid, which was allowed to react with thionyl chloride in an excessive amount under reflux for 6 hours and distilled for removing unaltered thionyl chloride to obtain the acid chloride in an amount of 0.9 g.

0.8 g of (R)-(+)-1-trifluoromethyl-2-ethoxycarbonylethyl 4-hydroxybenzoate obtained in 2), 0.3 g of triethylamine and 0.1 g of dimethylaminopyridine were dissolved in 50 ml of methylene chloride for preparing a solution, which was added to a solution of the acid chloride obtained in the above in 20 ml of methylene chloride for reaction at the room temperature, for a whole day and night.

The reaction liquid was poured into ice-water and extracted with methylene chloride. The methylene chloride phase was successively washed with diluted hydrochloric acid, water, 1N sodium carbonate solution and water. The organic phase was dried over anhydrous sodium sulphate and distilled for separating the crude compound.

The crude compound was subjected to silica gel chromatography with using hexane/ethylacetate as developer so as to obtain purified objective compound ([α]$_D^{20}$= +24.5°) in an amount of 0.5 g.

The phase transition temperatures thereof are as follows as a result of the observation by means of a polarizing microscope with a hot stage.

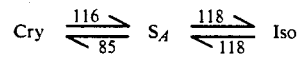

Figure 3:
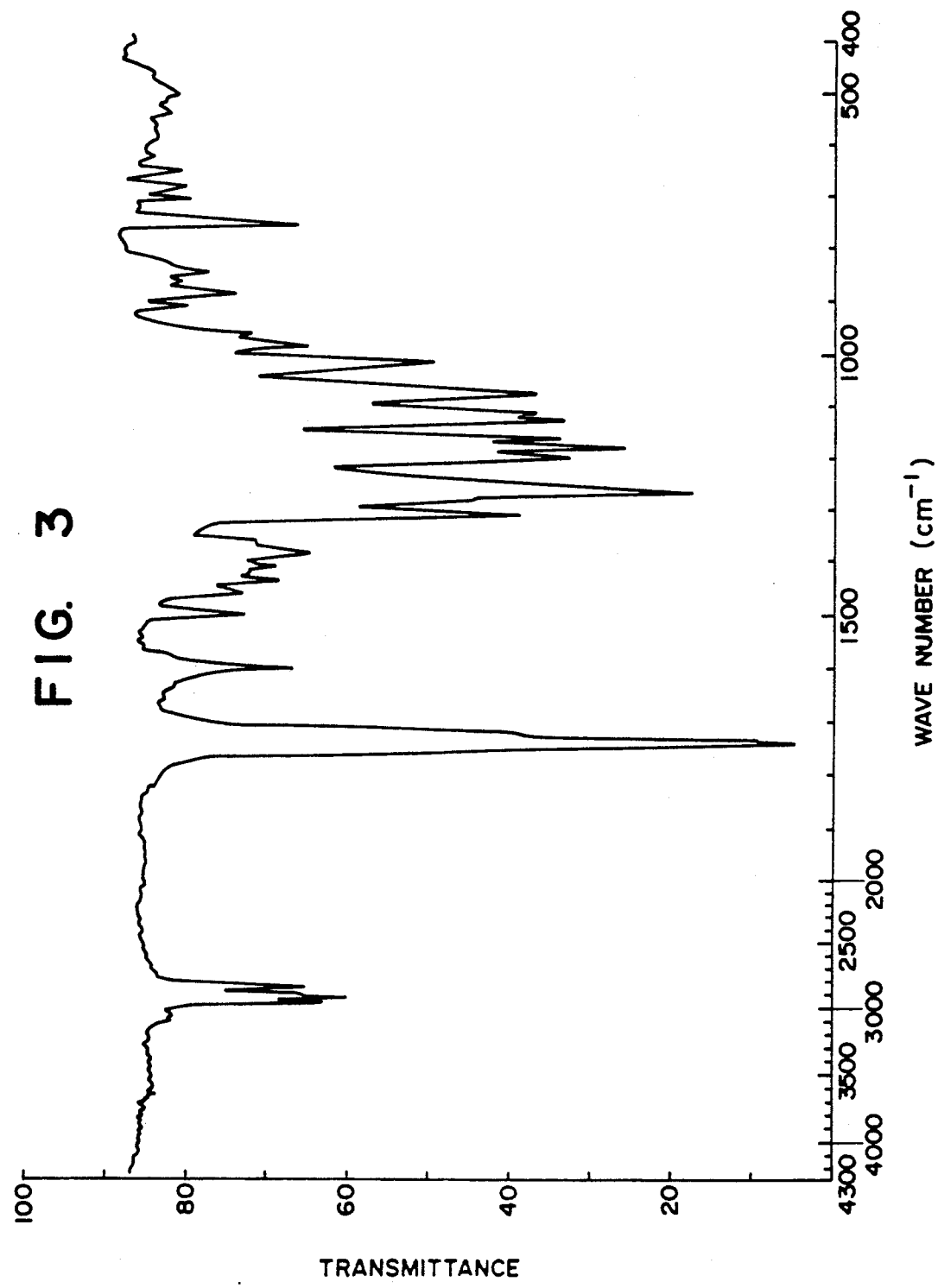
FIG. 3 shows the spectrum of (R)-(+)-4-(1-trifluoromethyl-2-ethoxycarbonyloxycarbonyl-)phenyl 4-(5-n-pentyl-trans-1,3-dioxane-2-yl)benzoate, the objective compound in Example 3.

The infrared absorption spectrum (KBr) is shown in FIG. 3.

EXAMPLE 4

1) Synthesis of 1-trifluoromethylheptyl 4'-hydroxybiphenyl-4-carboxylate

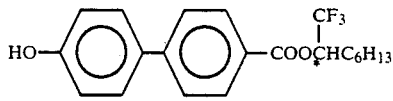

Example 1 was repeated except that 4'-benzyloxybiphenyl-4-carboxylic acid (5.0 g) was used in place of the 4-benzyloxybenzoic acid in 1) and 2) to prepare the above compound.

2) Synthesis of 4-(5-n-nonyl-1,3-dioxane-2-yl)benzoyl chloride

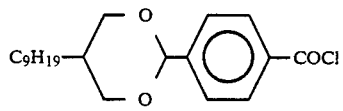

A solution of 2-(4-carboxyphenyl)-5-n-nonyl-1,3-dioxane (2.00 g) in thionyl chloride (10 g) was heated under refluxing for 4 hours with a small amount of N,N-dimethylformamide. Excessive amount of thionyl chloride was distilled to obtain the titled compound.

3) Synthesis of 4'-(1-trifluoromethylheptyloxycarbonyl)biphenyl-4-(5-n-nonyl-1,3-dioxane-2-yl)benzoate

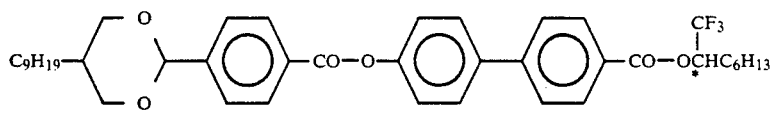

Figure 5:
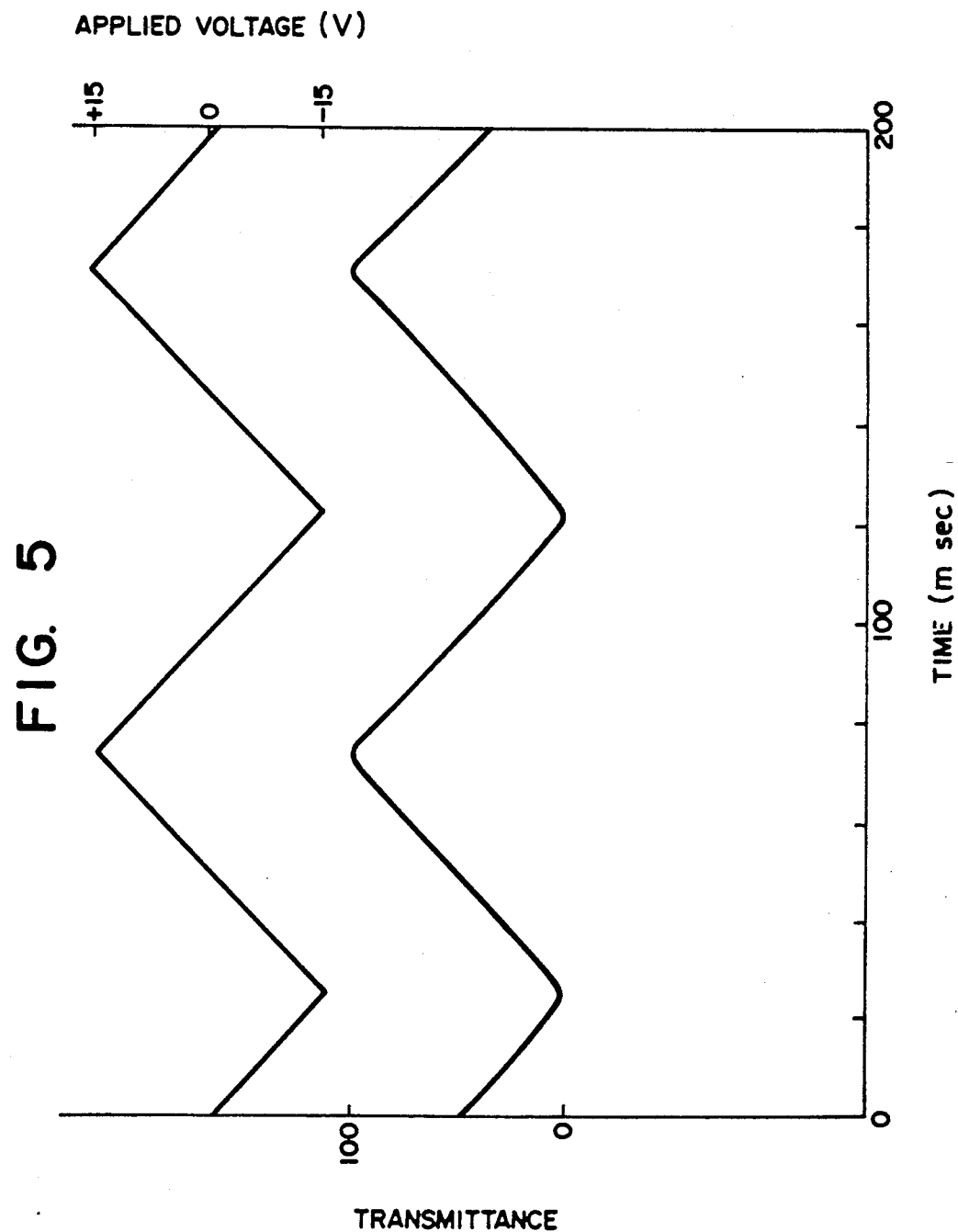
FIG. 5 shows an optical response wave form to an applied voltage of the objective compound in Example 3 according to the electroclinic effect in the $S_A$ phase.

To a solution of the carboxylate prepared in 1) above (0.96 g) and triethylamine (0.29 g) in dichloromethane (40 ml) was added drop by drop a solution of the chloride (1.14 g) prepared in 2) above in dichloromethane (40 ml). To the solution was added dimethylaminopyridine (0.10 g). The solution obtained was stirred at room temperature for one day. The solution was poured in water and the aqueous solution was neutralized. The dichloromethane was separated by a separating funnel. The dichloromethane separated was dried over anhydrous magnesium sulfate before being subjected to distillation. The residue was subjected to silica gel chromatography (developer:n-hexane/ethyl acetate=20/1) to obtain the titled compound (0.30 g). Phase transition temperatures (°C.) of the compound observed under a polarizing microscope with a hot stage are as follows:

electrooptical response behavier, whereby the electroclinic effect making optical response to the impressed electric field at the $S_A$ phase was confirmed as shown in FIG. 5.

EXAMPLE 6

Figure 6:
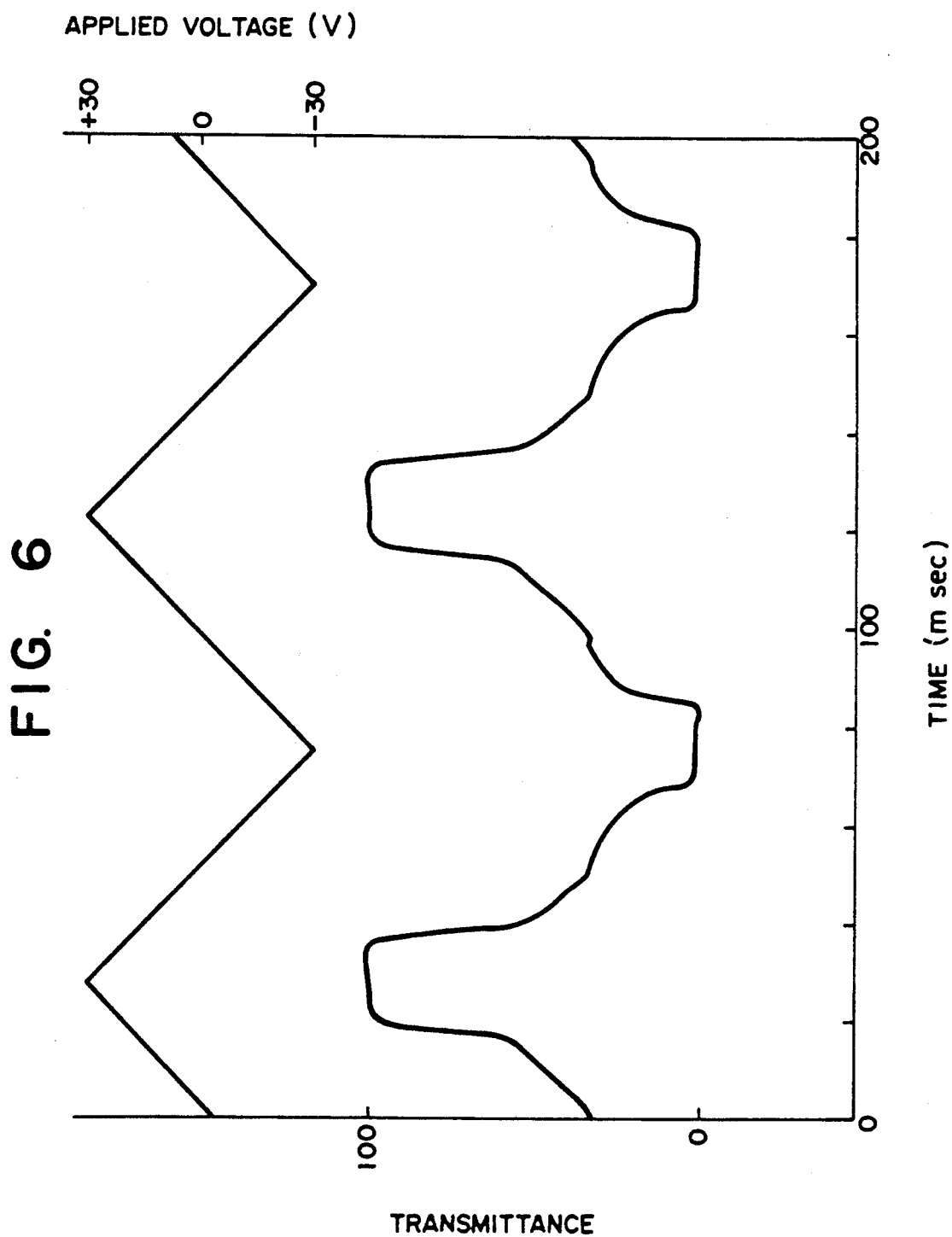
FIG. 6 shows an optical response wave form to an applied voltage of the objective compound in Example 2 in the $S_{(3)}^*$ phase.

The similar liquid crystal cell except that the liquid crystal obtained in Example 2 was used in place of that of Example 3 was mounted in the polarizing microscope having the photomultiplier of two polarizing plates so arranged as to make a right angle with each other in such a way that the molecular apsis makes an angle of 22.5° relative to the polarizer. This liquid crystal cell was gradually cooled at a temperature gradient of 0.1°–1.0° C./min to be in the S*c phase. In the range of a temperature of 70.0° C. to 18.0° C., a triangular wave voltage of ±30 V, 10 Hz was impressed, of which state is shown in FIG. 6, from which it is possible to observe tristable liquid crystal molecular orientations comprising a dark phase in case of minus impressed voltage, a medium phase in case of zero voltage and a light phase in case of the plus voltage.

TABLE 1

$CH_3CH_2CH_2(CH_2)_4CH_2CH_2$— [dioxane]—[phenyl]—$\overset{O}{\underset{\|}{C}}O$—[phenyl]—$\overset{O}{\underset{\|}{C}}O\overset{CF_3}{\underset{|}{C}}HCH_2CH_2CH_2CH_2CH_2CH_3$ A B C D E F G  IJ  K L  M N  O  P Q  R  S T U V W B A  (with H below dioxane)

| Carbon | ppm | Remarks | Carbon | ppm | Remarks |
| --- | --- | --- | --- | --- | --- |
| A | 14.0 | Methyl Carbon | O | 155.2 | Aromatic Carbon Adjacent to O |
| B | 22.5 | Methylene Carbon | P | 122.0 | Aromatic Ring Carbon |
| C | 31.9 | " | Q | 131.6 | " |
| D | 29.5 | " | R | 126.4 | Aromatic Ring Carbon Adjacent to Carbonyl |
| E | 26.4 | " | | | |
| F | 28.2 | " | S | 124.0 | $F_3$ Substituted Methyl Carbon |
| G | 34.2 | Methine Carbon | T | 70.3 | Methine Carbon Adjacent to $F_3$ Substituted Methyl |
| H | 72.6 | Methylene Carbon Adjacent to O | U | 24.6 | Methyl Carbon |
| I | 100.5 | Methine Carbon Adjacent to O | V | 28.8 | " |
| J | 144.3 | Aromatic Ring Carbon | W | 31.5 | " |
| K | 126.5 | " | | | |
| L | 130.1 | " | | | |
| M | 129.2 | Aromatic Ring Carbon Adjacent to Carbonyl | | | |
| N | 164.1 | Carbonyl Carbon | | | |

Figure 4:
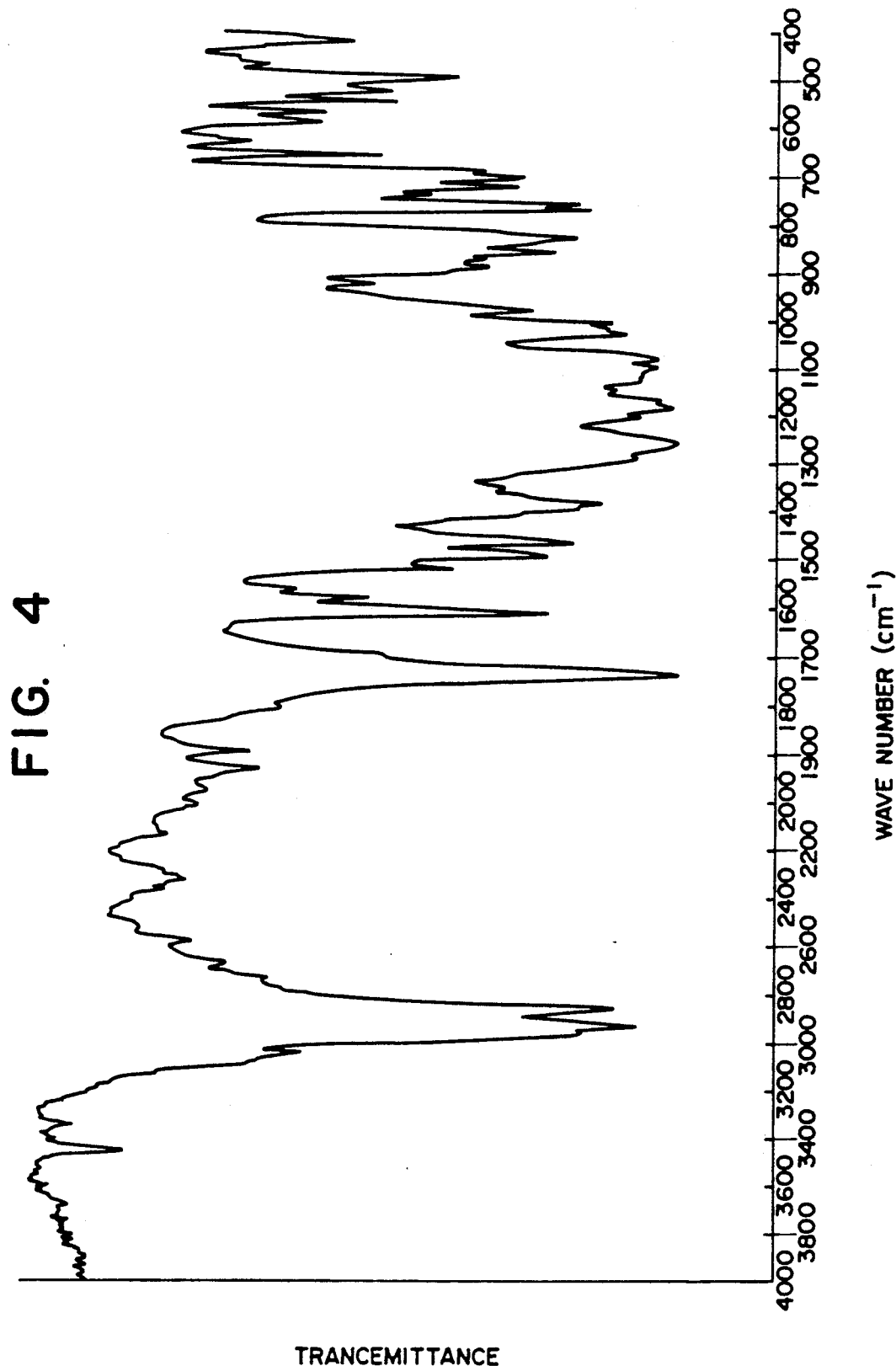
FIG. 4 shows the spectrum of 4'-(1-trifluoromethyl-heptyloxycarbonyl)biphenyl 4-(5-n-nonyl-1,3-dioxan-2-yl)benzoate, the objective compound in Example 4.

Crystal $\underset{\leq 40}{\overset{60.8}{\rightleftarrows}}$ Sx $\underset{90.8}{\overset{91.8}{\rightleftarrows}}$ S*(3) $\underset{118.9}{\overset{119.0}{\rightleftarrows}}$ $S_A$ $\underset{186.1}{\overset{187.6}{\rightleftarrows}}$ Iso The infrared absorption spectrum (KBr) is shown in FIG. 4.

EXAMPLE 5

In a liquid crystal cell casing of 2.3 μm thickness having an indium/tinoxide substrate coated with an orientated polyimide layer, the liquid crystal compounds obtained in Example 3 was filled in the isotropic phase to prepare a liquid crystal cell.

The cell was gradually cooled by a temperature gradient of 0.1°–1.0° C./min so that the liquid crystal was orientated at the $S_A$ phase, impressed voltage with a wave of ±15 V and 10 Hz and observed by a polarizing microscope having a photomultiplier so as to detect the

We claim:
1. A ferroelectric liquid crystal compound represented by the formula (I)

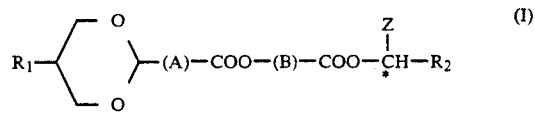

wherein (A) and (B) each independently means

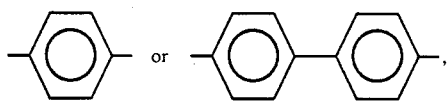

$R_1$ means a $C_1$–$C_{20}$ alkyl group, $R_2$ means a group selected from a group consisting of a $C_4$–$C_{12}$ alkyl group and an ester-containing group which is represented by the formula —$R_3COOR_4$ wherein $R_3$ is a $C_1$–$C_2$ alkylene group and $R_4$ is a $C_1$–$C_4$ alkyl group and Z means $CF_3$ or $C_2F_5$.

2. An antiferroelectric liquid crystal compound represented by the formula (II), which shows optically tristable states in $S^*_{(3)}$ phase

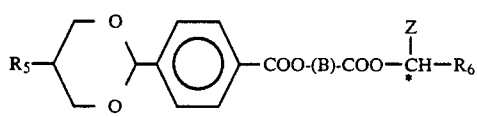

wherein (B) means

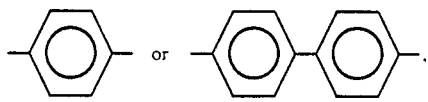

$R_5$ and $R_6$ each independently means a $C_5$–$C_{10}$ alkyl group and Z means $CF_3$ or $C_2F_5$.

3. An antiferroelectric liquid crystal compound in claim 2, where (B) means a group, which shows optically tristable states in $S^*_{(3)}$ phase.

4. An antiferroelectric liquid crystal compound in claim 2, wherein (B) means a group, which shows optically tristable states in $S^*_{(3)}$ phase.

5. An antiferroelectric liquid crystal compound in claim 2, wherein Z means a $CF_3$, which shows optically tristable states in $S^*_{(3)}$ phase.

6. An antiferroelectric liquid crystal compound in claim 3, wherein Z means a $CF_3$, which shows optically tristable states in $S^*_{(3)}$ phase.

7. An antiferroelectric liquid crystal compound in claim 4, wherein Z means a $CF_3$, which shows optically tristable states in $S^*_{(3)}$ phase.

8. An antiferroelectric liquid crystal compound represented by the formula (III), which shows optically tristable states in $S^*_{(3)}$ phase

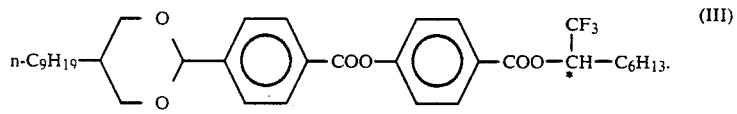

9. An antiferroelectric liquid crystal compound represented by the formula (IV), which shows optically tristable states in $S^*_{(3)}$ phase

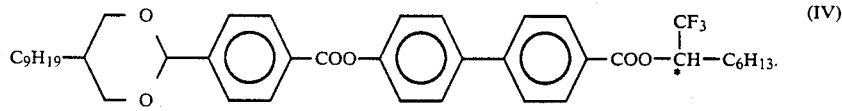

* * * * *